US009795277B2

(12) United States Patent
Fujita et al.

(10) Patent No.: US 9,795,277 B2
(45) Date of Patent: Oct. 24, 2017

(54) MONITOR APPARATUS (71) Applicant: OLYMPUS CORPORATION, Tokyo (JP)

(72) Inventors: Masaya Fujita, Sagamihara (JP); Masahiro Kudo, Hino (JP); Masashi Umemura, Hamburg (DE); Hiroshi Yanagisawa, Kawasaki (JP); Hiroshi Higuchi, Yamato (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/982,543

(22) Filed: Dec. 29, 2015

(65) Prior Publication Data
US 2016/0128546 A1 May 12, 2016

Related U.S. Application Data (63) Continuation of application No. PCT/JP2014/067968, filed on Jul. 4, 2014.

(30) Foreign Application Priority Data

Jul. 5, 2013 (JP) ................................. 2013-142093

(51) Int. Cl.
A61B 1/06 (2006.01)
A61B 1/00 (2006.01)
A61B 1/04 (2006.01)

(52) U.S. Cl.
CPC ........ A61B 1/00048 (2013.01); A61B 1/0005 (2013.01); A61B 1/00009 (2013.01);
(Continued)

(58) Field of Classification Search
CPC . A61B 1/00048; A61B 1/0018; A61B 1/0039; A61B 1/00045; A61B 1/0005
(Continued)

(56) References Cited

U.S. PATENT DOCUMENTS

2002/0085091 A1* 7/2002 Takeshige .............. H04N 7/183
348/65
2004/0225222 A1* 11/2004 Zeng ...................... A61B 1/043
600/476

(Continued)

FOREIGN PATENT DOCUMENTS

EP 1 870 827 A1 12/2007
JP H07-313450 A 12/1995

(Continued)

OTHER PUBLICATIONS

Oct. 7, 2014 International Search Report issued in International Patent Application No. PCT/JP2014/067968.

(Continued)

Primary Examiner — Anhtuan T Nguyen
Assistant Examiner — Jae Woo
(74) Attorney, Agent, or Firm — Oliff PLC (57) ABSTRACT A monitor apparatus includes: a display panel that displays a medical image; an as-viewed output terminal capable of outputting a video signal reflecting a same color set value as a color set value reflected in the medical image displayed on the display panel; a communication unit that detects device information regarding an external device connected to the as-viewed output terminal; and a second color setting reflection unit capable of controlling to further change the color set value reflected in the video signal outputted from the as-viewed output terminal based on a detection result of the communication unit.

7 Claims, 9 Drawing Sheets (52) U.S. Cl.
CPC ...... *A61B 1/00018* (2013.01); *A61B 1/00039* (2013.01); *A61B 1/00045* (2013.01); *A61B 1/04* (2013.01)

(58) Field of Classification Search
USPC .......................................................... 600/160
See application file for complete search history.

(56) References Cited

U.S. PATENT DOCUMENTS

| | | | | |
|---|---|---|---|---|
| 2006/0241418 | A1* | 10/2006 | Abe .................. | A61B 1/00009 600/433 |
| 2007/0015989 | A1* | 1/2007 | Desai ................ | A61B 1/00009 600/407 |
| 2007/0091170 | A1* | 4/2007 | Ota ................... | A61B 1/00045 348/65 |
| 2008/0122924 | A1* | 5/2008 | Tashiro .............. | G06F 19/327 348/51 |
| 2012/0004557 | A1* | 1/2012 | McDowall ......... | A61B 1/00186 600/476 |
| 2012/0013773 | A1* | 1/2012 | Yoshino ............ | A61B 1/0638 348/241 |
| 2012/0319006 | A1* | 12/2012 | Shida ................ | A61B 1/043 250/458.1 |
| 2013/0012794 | A1* | 1/2013 | Zeng ................. | A61B 1/00186 600/328 |
| 2014/0253703 | A1* | 9/2014 | King ................. | A61B 1/00057 348/65 |
| 2014/0375768 | A1* | 12/2014 | Tsuchiya ........... | A61B 1/00163 348/45 |
| 2015/0092090 | A1* | 4/2015 | Miura ............... | H04N 9/646 348/242 |

FOREIGN PATENT DOCUMENTS

| | | |
|---|---|---|
| JP | 2002-125219 A | 4/2002 |
| JP | 2002-200038 A | 7/2002 |
| JP | 2003-527880 A | 9/2003 |
| JP | 2003-339634 A | 12/2003 |
| JP | 2005-073721 A | 3/2005 |
| JP | 2007-111326 A | 5/2007 |
| JP | 2008-000282 A | 1/2008 |
| JP | 2012-020011 A | 2/2012 |
| WO | 00/57767 A2 | 10/2000 |

OTHER PUBLICATIONS

Aug. 4, 2015 Office Action issued in Japanese Patent Application No. 2015-503611.

* cited by examiner

MONITOR APPARATUS

CROSS REFERENCE TO RELATED APPLICATION

This application is a continuation application of PCT/JP2014/067968 filed on Jul. 4, 2014 and claims benefit of Japanese Application No. 2013-142093 filed in Japan on Jul. 5, 2013, the entire contents of which are incorporated herein by this reference.

BACKGROUND OF THE INVENTION

1. Field of the Invention

The present invention relates to a monitor apparatus.

2. Description of the Related Art

In recent years, medical systems, such as an endoscopic operation system for using an endoscope to perform a procedure, are widely used, and a wide variety of medical devices are employed.

An example of a known medical system arranged in an operating room includes an endoscopic operation system illustrated in Japanese Patent Application Laid-Open Publication No. 2012-020011, the endoscopic operation system including: a cart provided with various medical devices, such as a camera apparatus for endoscope connected with an endoscope, a light source apparatus, and an image recording apparatus, and including a display apparatus, such as a TV monitor, that displays an endoscopic image and the like; and a patient bed.

In recent years, an apparatus is also known that receives video signals from a medical image shooting apparatus and the like called medical modalities in addition to endoscopic image signals and that displays the video signals from the medical modalities on the display apparatus in the endoscopic operation system along with the endoscopic images.

Note that examples of the medical modalities include MRI, CT, and an ultrasound endoscope, and other examples include a patient monitor apparatus and a fluoroscopic apparatus that output biological information.

A system is also proposed, in which the video signals from the modalities, such as MRI and CT, are supplied from an image saving and communication system terminal called PACS (picture archiving and communication system).

On the other hand, a monitor is proposed as a display apparatus in the endoscopic operation system in recent years, in which an internal image processing section can change a color set value and the like of an image to be displayed.

In this type of monitor, the internal image processing section enables processing of changing a resolution or changing a screen display mode (for example, changing between a one-screen display mode and a two-screen display mode) in addition to the processing of changing the color set value of the image, regardless of an external image processing apparatus.

SUMMARY OF THE INVENTION

A monitor apparatus according to one aspect of the present invention is a monitor apparatus that is configured as a separate body from at least a video processor including a medical image processing section, and includes a housing in which a display section that displays a predetermined medical image is disposed, the monitor apparatus including: the display section that displays a medical image; a plurality of medical image signal input sections disposed in the housing of the monitor apparatus including the display section, each of the plurality of medical image signal input sections being capable of receiving a predetermined medical image signal including a medical image signal outputted from the video processor; a signal processing section that is disposed in the housing of the monitor apparatus and applies predetermined signal processing to the medical image signal inputted to each of the medical image signal input sections, to generate a video signal to be displayed on the display section; a first color setting section that is disposed in the housing of the monitor apparatus and executes processing of reflecting a predetermined first color set value on the video signal to be displayed on the display section which has been generated by the signal processing section; a second color setting section that is disposed in the housing of the monitor apparatus and executes at least processing of reflecting a second color set value on the video signal to be displayed on the display section which has been generated by the signal processing section, the second color set value being a same color set value as the first color set value in the first color setting section; a video signal output section that is disposed in the housing of the monitor apparatus, the video signal output section being connected with at least one or more external devices and capable of outputting the video signal outputted from the second color setting section; and an external device information detecting section that is disposed in the housing of the monitor apparatus and detects device information regarding a type of the external device connected to the video signal output section, wherein the second color setting section is capable of executing: first mode processing for reflecting the second color set value, which is the same color set value as the first color set value in the first color setting section, on the video signal to be displayed on the display section which has been generated by the signal processing section, to cause the video signal output section to output the video signal; second mode processing for causing the video signal output section to output the video signal to be displayed on the display section which has been generated by the signal processing section, without reflecting any color setting processing on the video signal; and third mode processing for reflecting a third color set value set according to color set value information included in the external device connected to the video signal output section, in addition to the second color set value, on the video signal to be displayed on the display section which has been generated by the video signal processing section, when the external device has a color setting function different from the first color set value, based on a detection result by the external device information detecting section, to cause the video signal output section to output the video signal.

DETAILED DESCRIPTION OF THE PREFERRED EMBODIMENTS

Hereinafter, embodiments of the present invention will be described with reference to the drawings.

First Embodiment

Figure 1:
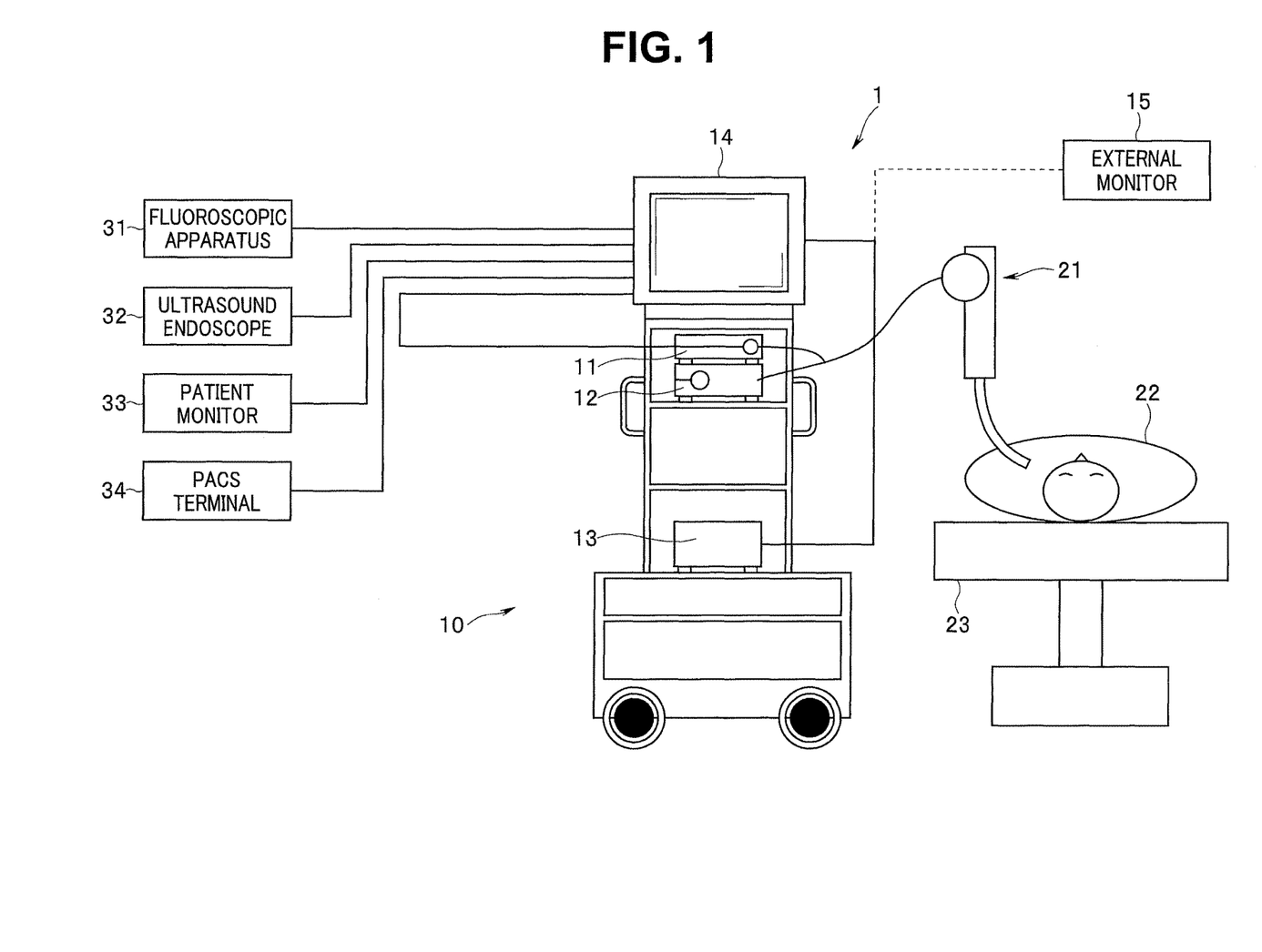
FIG. 1 is a diagram showing an entire configuration of an endoscopic operation system according to a first embodiment of the present invention.

FIG. 1 is a diagram showing an entire configuration of an endoscopic operation system according to a first embodiment of the present invention.

As shown in FIG. 1, an endoscopic operation system 1 according to the first embodiment of the present invention is a medical system arranged in, for example, an operation room. The endoscopic operation system 1 includes a cart 10 provided with various medical devices and the like described later and includes a patient bed 23.

The cart 10 is provided with apparatuses, such as a video processor 11, a light source apparatus 12, and a recording apparatus 13, which are medical devices to be controlled. The video processor 11 and the light source apparatus 12 are connected to an endoscope 21 through a universal cord.

The cart 10 is also provided with a monitor apparatus 14 that displays an endoscopic image and the like and that includes, for example, a liquid crystal display.

The monitor apparatus 14 is connected to the video processor 11 and displays an endoscopic image outputted from the video processor 11. A plurality of medical modalities are connected to the monitor apparatus 14.

Examples of the medical modalities include a fluoroscopic image output apparatus 31 of X-ray, MRI, or the like, an ultrasound endoscope 32, a patient monitor apparatus 33 that outputs biological information of patient, and a terminal apparatus 34 of so-called PACS (picture archiving and communication system). In the present embodiment, image signals (or information signals) from these various medical modalities are inputted to respective video input sections of the monitor apparatus 14.

Figure 2:
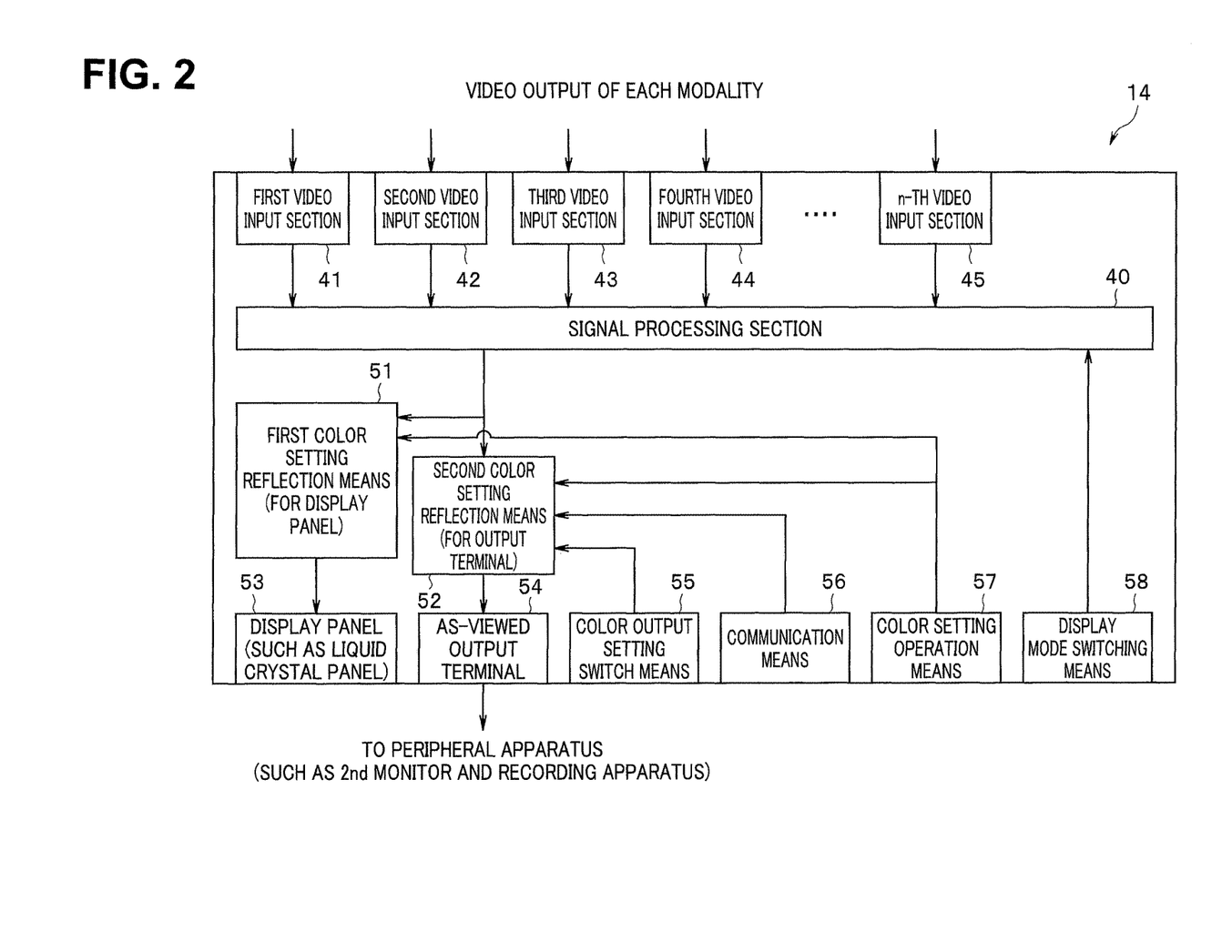
FIG. 2 is a block diagram showing an electrical internal configuration of a monitor apparatus in the endoscopic operation system according to the first embodiment of the present invention.

FIG. 2 is a block diagram showing an electrical internal configuration of the monitor apparatus in the endoscopic operation system according to the first embodiment.

As shown in FIG. 2, the monitor apparatus 14 includes a plurality of video input sections (a first video input section 41, a second video input section 42, a video input section 43, a fourth video input section 44, . . . and an n-th video input section 45) that receive the image signals (or information signals) from the various medical modalities and also includes: a display panel 53 including a liquid crystal panel or the like; and a signal processing section 40 that applies predetermined signal processing to each of the image signals inputted to the plurality of video input sections to generate video signals to be displayed on the display panel 53.

The monitor apparatus 14 further includes display mode switching means 58 for switching a display mode and the like through operation by an operator. The display mode switching means 58 is connected to the signal processing section 40, and the display mode switching means 58 can be operated to switch the plurality of video input sections (the first video input section 41, the second video input section 42, the video input section 43, the fourth video input section 44, . . . and the n-th video input section 45) or to switch display patterns (for example, switching operation of one-screen display and two-screen display (or multiple-screen display)).

The signal processing section 40 applies predetermined signal processing, synthesizing processing, or the like to an image signal inputted to one of the plurality of video input sections 41 . . . 45 or to image signals inputted to a plurality of video input sections according to the switching operation of the display mode switching means 58 and generates a video signal to be displayed on the display panel 53.

The monitor apparatus 14 further includes first color setting reflection means 51 for applying predetermined color adjustment (color setting) to the video signal after the predetermined signal processing by the signal processing section 40 and for reflecting information of the color setting in an image displayed on the display panel 53.

The monitor apparatus 14 further includes color setting operation means 57 for performing the color adjustment in the first color setting reflection means 51 through operation by the operator. The first color setting reflection means 51 applies predetermined color adjustment (color setting) to the video signal after the predetermined signal processing by the signal processing section 40, according to the operation of the color setting operation means 57.

On the other hand, the monitor apparatus 14 of the present embodiment includes an output terminal 54 (hereinafter, referred to as "as-viewed output terminal 54") that outputs a video exactly the same as the video outputted from the signal processing section 40 to the display panel 53.

The monitor apparatus 14 further includes second color setting reflection means 52 with a function similar to the first color setting reflection means 51, that is, the second color setting reflection means 52 is for applying predetermined color adjustment (color setting) to the video signal after the predetermined signal processing by the signal processing section 40 and for outputting an output signal reflecting information of the color setting to the as-viewed output terminal 54.

The color setting operation means 57 is also connected to the second color setting reflection means 52. That is, like the first color setting reflection means 51, the second color setting reflection means 52 is configured to apply predetermined color adjustment (color setting) to the video signal after the predetermined signal processing by the signal processing section 40, according to the operation of the color setting operation means 57.

In this way, the same video signal after the predetermined signal processing by the signal processing section 40 is outputted to both of the display panel 53 and the as-viewed output terminal 54 in the present embodiment.

Through the operation of the color setting operation means 57, the first color setting reflection means 51 and the second color setting reflection means 52 perform similar color adjustment (color setting), and the same color adjustment (color setting) is applied to the video signals outputted to both of the "display panel 53" and the "as-viewed output terminal 54".

Therefore, when the color setting operation means 57 is operated to perform the predetermined color adjustment (color setting) in the monitor apparatus 14 of the endoscopic operation system according to the present embodiment, the video signal of the same image as the image after the color setting displayed on the display panel 53 can be outputted from the as-viewed output terminal 54 to an external recording apparatus or to a peripheral apparatus such as an external monitor apparatus.

Furthermore, in the endoscopic operation system of the present embodiment, the display mode switching means 58 is operated to output the same video signal after synthesis/switch of the video by the signal processing means (signal processing section 40) in the monitor apparatus 14 to both of the "display panel 53" and the "as-viewed output terminal 54" in a case of a multiple-display mode for displaying a plurality of images on one screen of the display panel 53 or in a case of switching and displaying images of the plurality of medical modalities. Therefore, the video signal to be outputted to a recording apparatus or to a peripheral apparatus, such as an external monitor apparatus, can be easily switched without reconnecting a video output cable.

Here, a problem in outputting, from the "as-viewed output terminal 54", the video signal reflecting the "same color setting" as the color setting reflected in the video signal displayed on the "display panel 53" will be described.

As described, a technical scope of outputting, from the "as-viewed output terminal 54", the video signal reflecting the "same color setting" as the color setting reflected in the video signal displayed on the "display panel 53" according to the present invention attains a great amount of effects. However, the technical scope has a new problem illustrated below.

Figure 4:
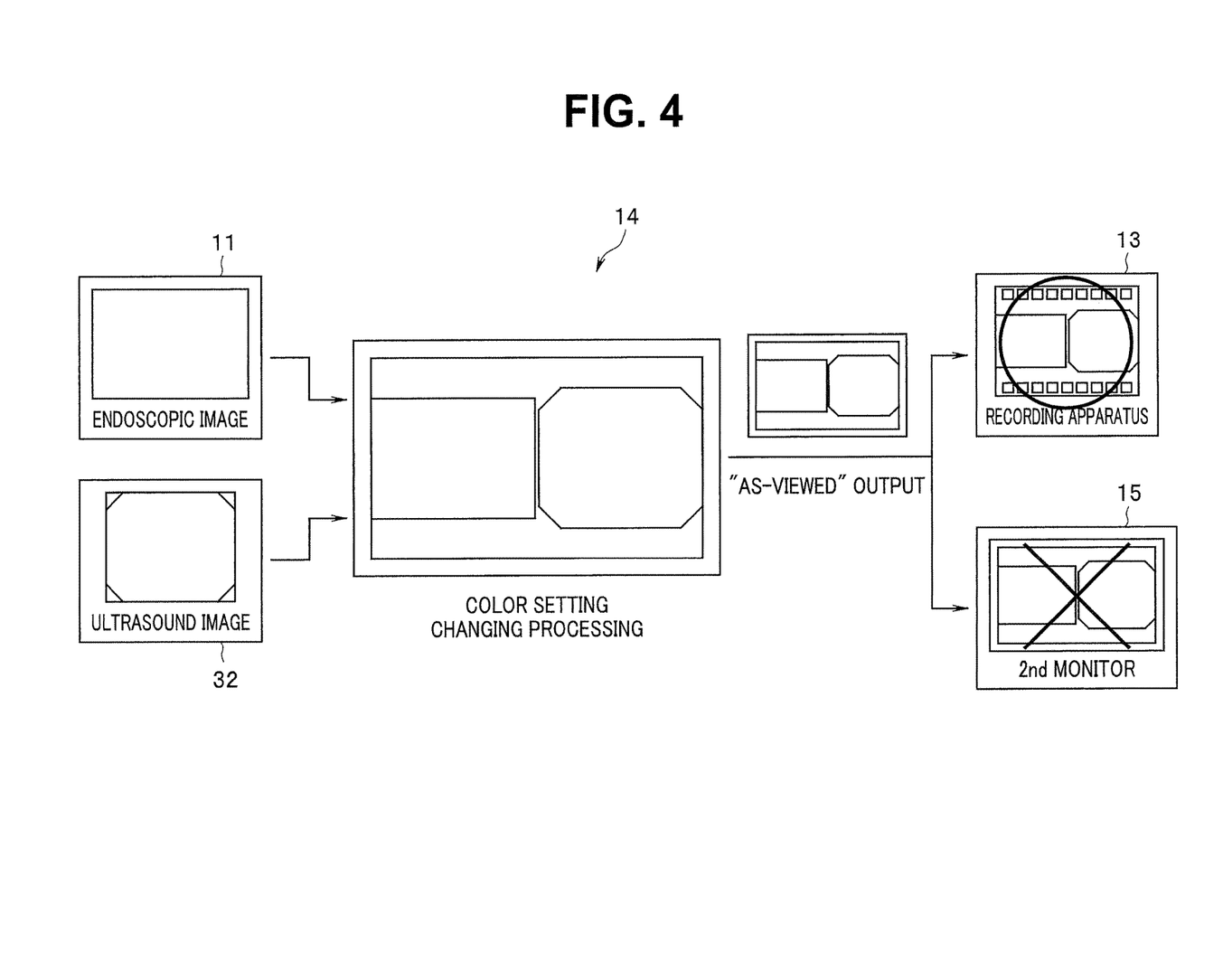
FIG. 4 is an explanatory diagram showing a situation in outputting an "as-viewed" signal from the monitor apparatus in the endoscopic operation system according to the first embodiment of the present invention.
Figure 5:
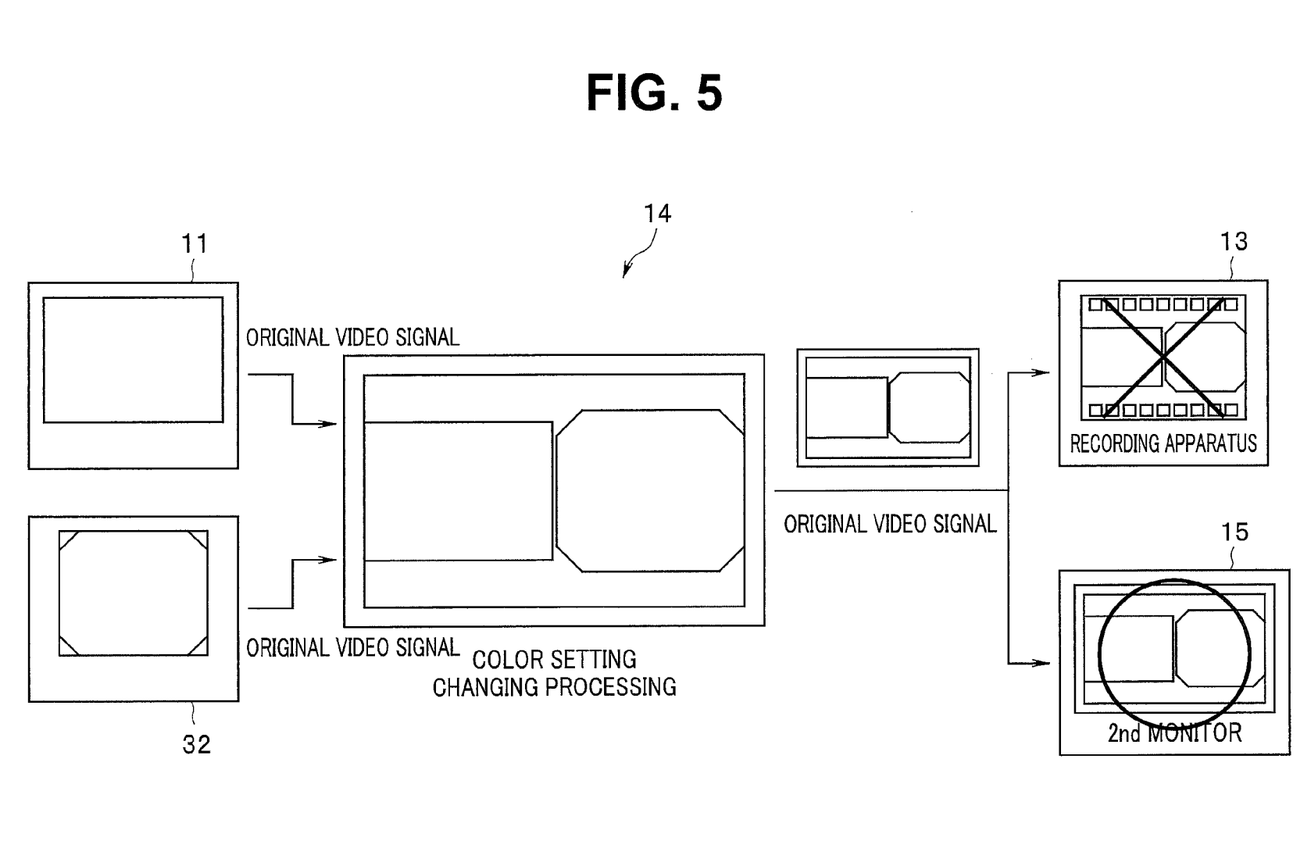
FIG. 5 is an explanatory diagram showing a situation in outputting an original video signal of the monitor apparatus in the endoscopic operation system according to the first embodiment of the present invention.

FIG. 4 is an explanatory diagram showing a situation in outputting the "as-viewed" signal from the monitor apparatus in the endoscopic operation system according to the first embodiment. FIG. 5 is an explanatory diagram showing a situation in outputting an original video signal (video signal from each modality) of the monitor apparatus in the endoscopic operation system according to the first embodiment.

In the circumstances shown in FIG. 4, the monitor apparatus 14 first synthesizes an endoscopic image from the video processor 11 and an ultrasound image from the ultrasound endoscope 32 to perform two-screen display, and the first color setting reflection means 51 and the second color setting reflection means 52 further perform the "same color setting". The video signal reflecting the "same color setting" as the video signal displayed on the display panel 53 is outputted from the as-viewed output terminal 54.

In this case, the video signal reflecting the "same color setting" as the video signal displayed on the display panel 53 can be recorded as it is in the recording apparatus 13 connected to the as-viewed output terminal 54, and this is useful. However, the following problem may occur when the same video signal is displayed on another external monitor (2nd monitor) 15.

That is, assuming that the external monitor (2nd monitor) is, for example, a monitor of a personal computer, predetermined various set values can also be changed in the external monitor in many cases.

In this case, various settings doubly affect the video signal outputted from the as-viewed output terminal 54 of the monitor apparatus 14, and a problem may occur in some cases, such as a large color shift from the image in the "as-viewed" state.

On the other hand, as shown in FIG. 5, if video signals not reflecting the color settings in the first color setting reflection means 51 and the second color setting reflection means 52, that is, original video signals, are outputted from the as-viewed output terminal 54, there is no inconvenience for the external monitor as described above. However, the video signals are obviously not an image in the "as-viewed" state, and an expected object may not be attained in consideration of recording the image in the recording apparatus 13.

In view of the circumstances, the present applicant switches the state of the video signal outputted from the "as-viewed output terminal 54" according to a connected output destination and provides the following solving means.

As described, the action of the second color setting reflection means 52 enables the monitor apparatus 14 in the endoscopic operation system according to the present embodiment to output, from the "as-viewed output terminal 54", the video signal reflecting the "same color setting" as the color setting reflected in the video signal displayed on the "display panel 53", and the second color setting reflection means 52 according to the present embodiment enables outputting of other types of video signals through the "as-viewed output terminal 54".

That is, the second color setting reflection means 52 enables outputting of the video signal in three modes: a first output mode (color output mode) for causing the "as-viewed output terminal 54" to output a video signal reflecting the "same color setting" as the color setting reflected in the video signal displayed on the "display panel 53"; a second output mode (through mode) for causing the "as-viewed output terminal 54" to output a video signal in a state not reflecting the color setting; and a third output mode (PC mode) for causing the "as-viewed output terminal 54" to output a video signal after predetermined color adjustment in addition to the color setting reflected in the video signal displayed on the "display panel 53" in order to reproduce a video signal suitable for replay in an external monitor when the output destination is, for example, the external monitor of a personal computer.

The second color setting reflection means 52 also includes a table used particularly in the third output mode (PC mode), the table storing color set value information that is set according to a predetermined device of the connection destination. When the third output mode (PC mode) is set, a color set value of the video signal to be outputted from the "as-viewed output terminal 54" is changed based on the table storing the set value information.

The monitor apparatus 14 according to the present embodiment includes communication means 56 for performing predetermined communication with an external peripheral device that is the output destination of the video signal.

The communication means 56 has a function of detecting the device of the connection destination through communication based on RS232C or through communication based on EDID (extended display identification data) storing model/specification information of the display, for example. The communication means 56 is configured to transmit the detection result information to the second color setting reflection means 52.

The second color setting reflection means 52 selects each of the modes of the video signal to be outputted from the "as-viewed output terminal 54" based on the information from the communication means 56.

Figure 3:
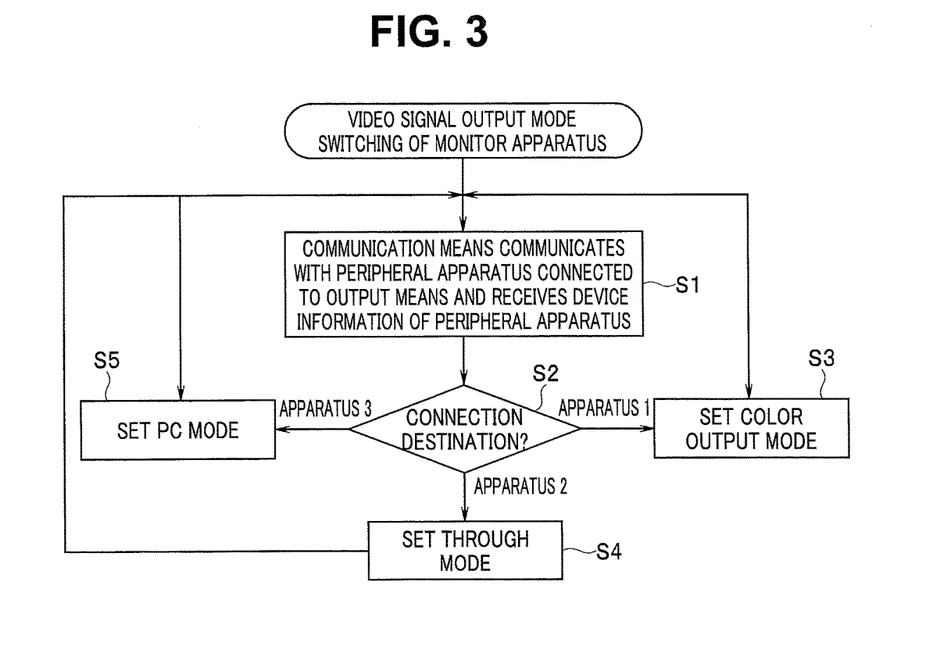
FIG. 3 is a flowchart showing a video signal output mode switch action of the monitor apparatus in the endoscopic operation system according to the first embodiment of the present invention.
Figure 6:
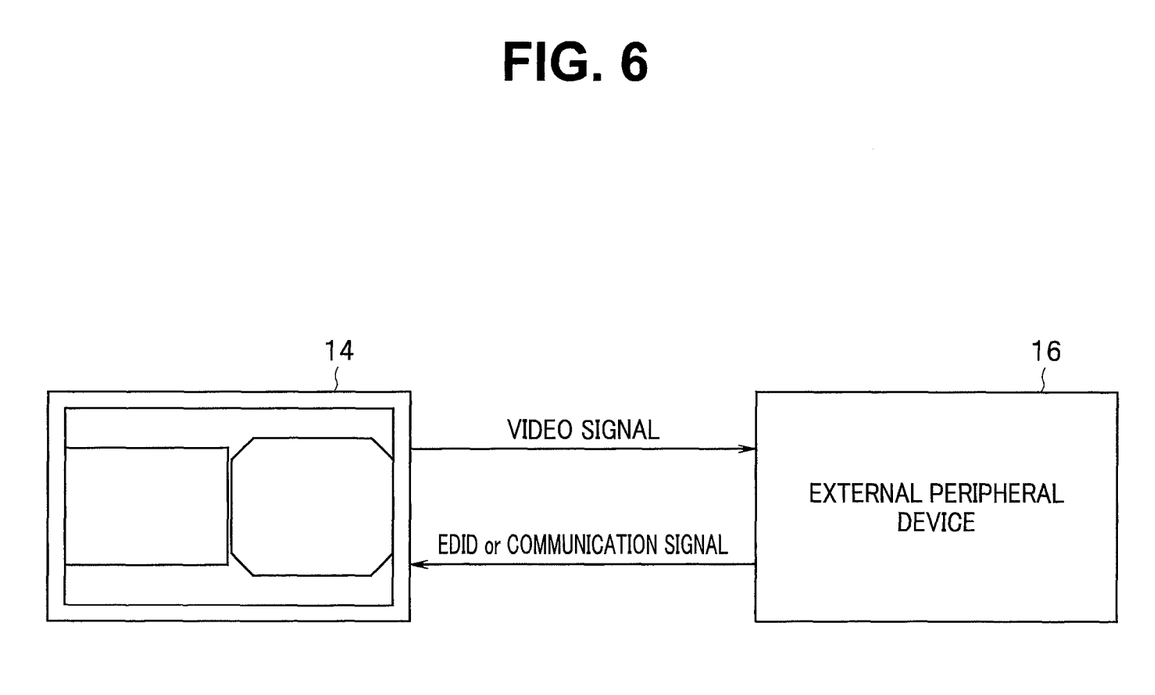
FIG. 6 is an explanatory diagram showing a situation when the monitor apparatus in the endoscopic operation system according to the first embodiment of the present invention detects a type of a video signal output destination.

FIG. 3 is a flowchart showing a video signal output mode switch action of the monitor apparatus in the endoscopic operation system according to the first embodiment. FIG. 6 is an explanatory diagram showing a situation when the monitor apparatus in the endoscopic operation system according to the first embodiment detects a type of the video signal output destination.

As shown in FIGS. 3 and 6, the communication means 56 in the monitor apparatus 14 first connects to the external peripheral device 16, then acquires the EDID of the external peripheral device 16 or receives the device information of the external peripheral device 16 through predetermined communication to detect the type of the device, and transmits the detection result information to the second color setting reflection means 52 (step S1, step S2).

Subsequently, if the external peripheral device 16 is, for example, the recording apparatus 13 based on the information from the communication means 56, the second color setting reflection means 52 sets the first output mode (color output mode) for causing the "as-viewed output terminal 54" to output the video signal reflecting the "same color setting" as the color setting reflected in the video signal displayed on the "display panel 53" (step S3).

On the other hand, if the external peripheral device 16 is an external monitor or the like that can change various set values, the second color setting reflection means 52 sets the second output mode (through mode) for causing the "as-viewed output terminal 54" to output the video signal in the state not reflecting the color setting (step S4).

If the external peripheral device 16 is, for example, an external monitor of a personal computer, and the storage table including the information for reproducing the video signal suitable for replay in the external monitor is acquired, the second color setting reflection means 52 sets the third output mode (PC mode) for causing the "as-viewed output terminal 54" to output the video signal after further predetermined color adjustment of the color setting reflected in the video signal displayed on the "display panel 53" based on the table storing the set value information (step S5).

Note that although the communication means 56 automatically detects the information of the external peripheral device at the connection destination of the as-viewed output terminal 54 in the description, the monitor apparatus 14 according to the present embodiment may include color output setting switch means 55 for the operator to manually switch the color setting, and the three output modes may be switched according to the operation of the color output setting switch means 55.

As described, according to the monitor apparatus 14 in the endoscopic operation system of the present embodiment, the video signal of the same image as the image after the color setting displayed on the display panel 53 can be outputted from the as-viewed output terminal 54 to an external recording apparatus or to a peripheral apparatus such as an external monitor apparatus.

Furthermore, according to the monitor apparatus 14 in the endoscopic operation system of the present embodiment, the same video signal after the synthesis/switch of the video by the signal processing means (signal processing section 40) in the monitor apparatus 14 is outputted to both of the "display panel 53" and the "as-viewed output terminal 54" in the case of the multiple-display mode for displaying a plurality of images on one screen of the display panel 53 or in the case of switching and displaying images of a plurality of the medical modalities. Therefore, the video signal to be outputted to a recording apparatus or to a peripheral apparatus, such as an external monitor apparatus, can be easily switched without reconnecting the video output cable.

Furthermore, according to the monitor apparatus 14 in the endoscopic operation system of the present embodiment, the set values of the color information values reflected in the video signal to be outputted can be changed according to the device information of the external peripheral device connected to the as-viewed output terminal 54 that outputs the video signal of the same image as the image after the color setting displayed on the display panel 53. Therefore, the video signal according to the type of the external peripheral device can be accurately outputted.

Next, a second embodiment of the present invention will be described.

In recent years, a monitor provided with an enhancement processing technique (processing technique such as a super-resolution technique) for emphasizing and displaying a sense of resolution in displaying a low-resolution video in an SD format or the like has come to be known as a display apparatus in the endoscopic operation system.

The enhancement processing technique is adapted to identify a color or a pattern of an entire screen to be displayed to control strength of the color or the pattern to thereby apply enhancement processing to the entire screen.

On the other hand, an apparatus is known that receives video signals from a medical image shooting apparatus and the like that are called medical modalities in addition to endoscopic image signals and that displays the video signals from the medical modalities on the display apparatus in the endoscopic operation system along with the endoscopic images.

In the display apparatus of this type, a two-screen function or the like can be used to display a plurality of medical modalities (for example, an endoscope, an ultrasound endoscope, and a fluoroscopic apparatus) with different colors or display contents on one screen.

However, when the enhancement processing is executed in a state that the images of the plurality of medical modalities are displayed on one screen in the display apparatus, there is an inconvenience that the images that should not be subjected to the enhancement processing are also enhanced and emphasized.

For example, when an endoscopic image is displayed as a main screen, and an ultrasound image or a fluoroscopic image is displayed as a sub screen, the enhancement processing may also be applied to the sub screens that should not be subjected to the enhancement processing.

Figure 7:
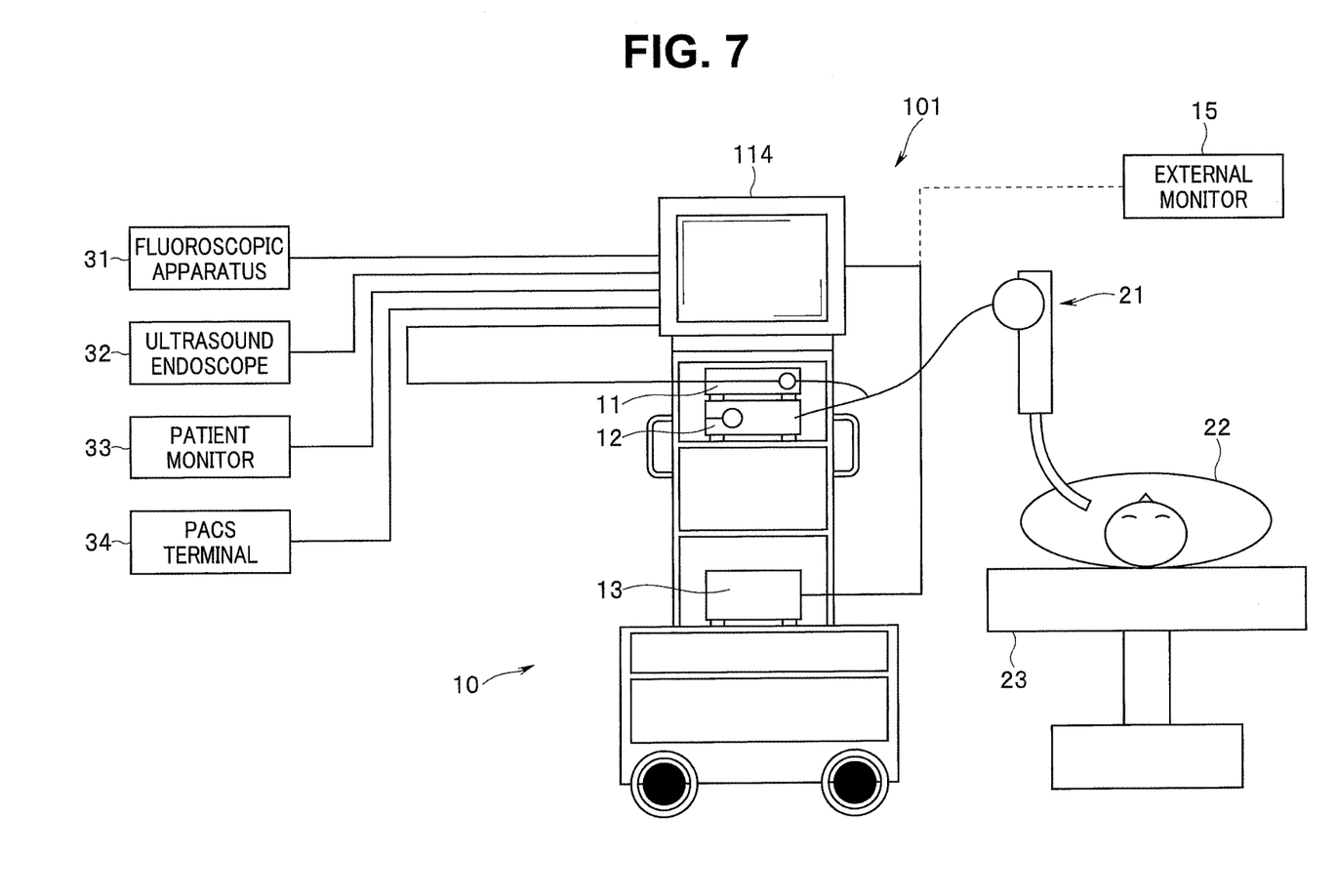
FIG. 7 is a diagram showing an entire configuration of an endoscopic operation system according to a second embodiment of the present invention.

In view of the circumstances, the present applicant provides a medical display apparatus that can set a range (area) for applying the enhancement processing according to the conditions of the display screen;

FIG. 7 is a diagram showing an entire configuration of an endoscopic operation system according to a second embodiment of the present invention.

As shown in FIG. 7, an endoscopic operation system 101 according to the second embodiment of the present invention has a configuration similar to the endoscopic operation system 1 according to the first embodiment, but a configuration of a monitor apparatus 114 is different. The other components are the same as in the first embodiment, and the details will not be repeated here.

The monitor apparatus 114 according to the present second embodiment is connected to the video processor 11 and displays an endoscopic image outputted from the video processor 11 as in the first embodiment. A plurality of medical modalities are connected to the monitor apparatus 114.

As in the first embodiment, examples of the medical modalities include the fluoroscopic image output apparatus 31 of X-ray, MRI, or the like, the ultrasound endoscope 32, the patient monitor apparatus 33 that outputs biological information of patient, and the terminal apparatus 34 of so-called PACS (picture archiving and communication system). Image signals (or information signals) from these various medical modalities are also inputted to respective video input sections of the monitor apparatus 114 in the present embodiment.

Figure 8:
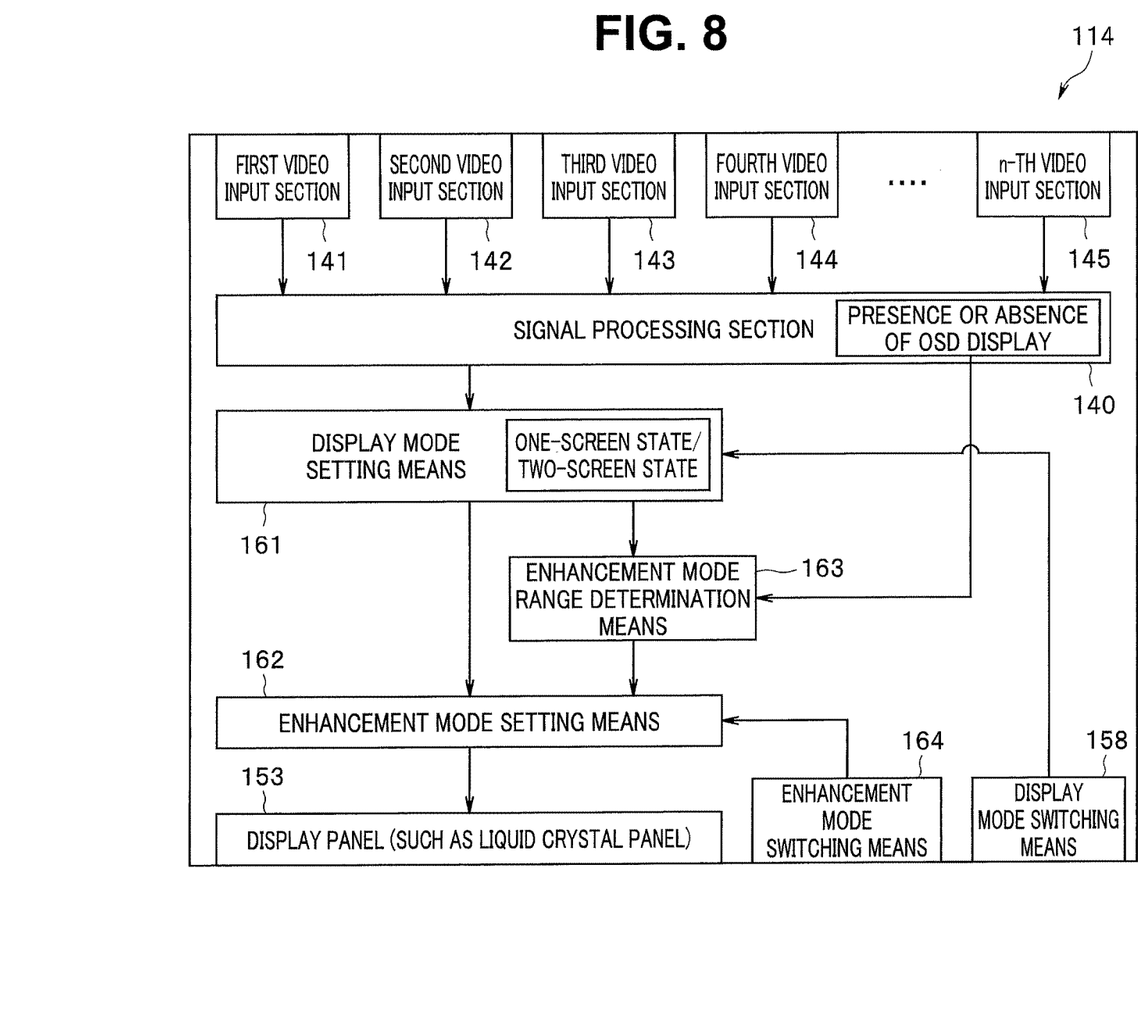
FIG. 8 is a block diagram showing an electrical internal configuration of a monitor apparatus in the endoscopic operation system according to the second embodiment of the present invention.

FIG. 8 is a block diagram showing an electrical internal configuration of the monitor apparatus 114 in the endoscopic operation system according to the second embodiment.

As shown in FIG. 8, the monitor apparatus 114 includes a plurality of video input sections (a first video input section 141, a second video input section 142, a video input section 143, a fourth video input section 144, . . . and an n-th video input section 145) that receive the image signals (or information signals) from the various medical modalities and also includes: a display panel 153 including a liquid crystal panel or the like; and a signal processing section 140 that applies predetermined signal processing to each of the image signals inputted to the plurality of video input sections to generate video signals to be displayed on the display panel 53.

The monitor apparatus 114 further includes display mode switching means 158 for switching a display mode and the like through operation by the operator and also includes display mode setting means 161 for switching and setting the display mode for the video signals generated by the signal processing section 140.

The display mode setting means 161 is configured to switch the plurality of video input sections (the first video input section 141, the second video input section 142, the video input section 143, the fourth video input section 144, . . . and the n-th video input section 145) or to switch display patterns (for example, switching operation of one-screen display state and two-screen display state (or multiple-screen display state)) according to the operation of the display mode switching means 158.

The monitor apparatus 114 further includes enhancement mode range determination means 163 for determining an enhancement mode range according to the display mode of the display mode setting means 161 and the state of the video signal of the signal processing section 140 (presence or absence of OSD display in the video signal displayed on the display panel 153) and also includes enhancement mode setting means 162 for applying predetermined enhancement processing to the range determined by the enhancement mode range determination means 163.

To prevent application of the enhancement processing to an area in which the enhancement processing is unnecessary (for example, sub screen in two-screen display and OSD menu), the enhancement mode range determination means 163 is configured to check the current state of the display mode in the display mode setting means 161 (one-screen display state or multiple-screen display state including two-screen) and presence or absence of the OSD display in the signal processing section 140 and is configured to determine the range (area) for applying the enhancement processing according to the result to report the range (area) to the enhancement mode setting means 162.

Enhancement mode switching means 164 for switching and setting the enhancement mode is connected to the enhancement mode setting means 162, and the enhancement mode setting means 162 is configured to set the enhancement mode according to the switching operation of the enhancement mode switching means 164.

Note that in the monitor apparatus 114 of the present embodiment, the enhancement mode setting means 162 is configured to apply the enhancement processing to the range determined by the enhancement mode range determination means 163 through predetermined enhancement processing operation not shown.

Figure 9:
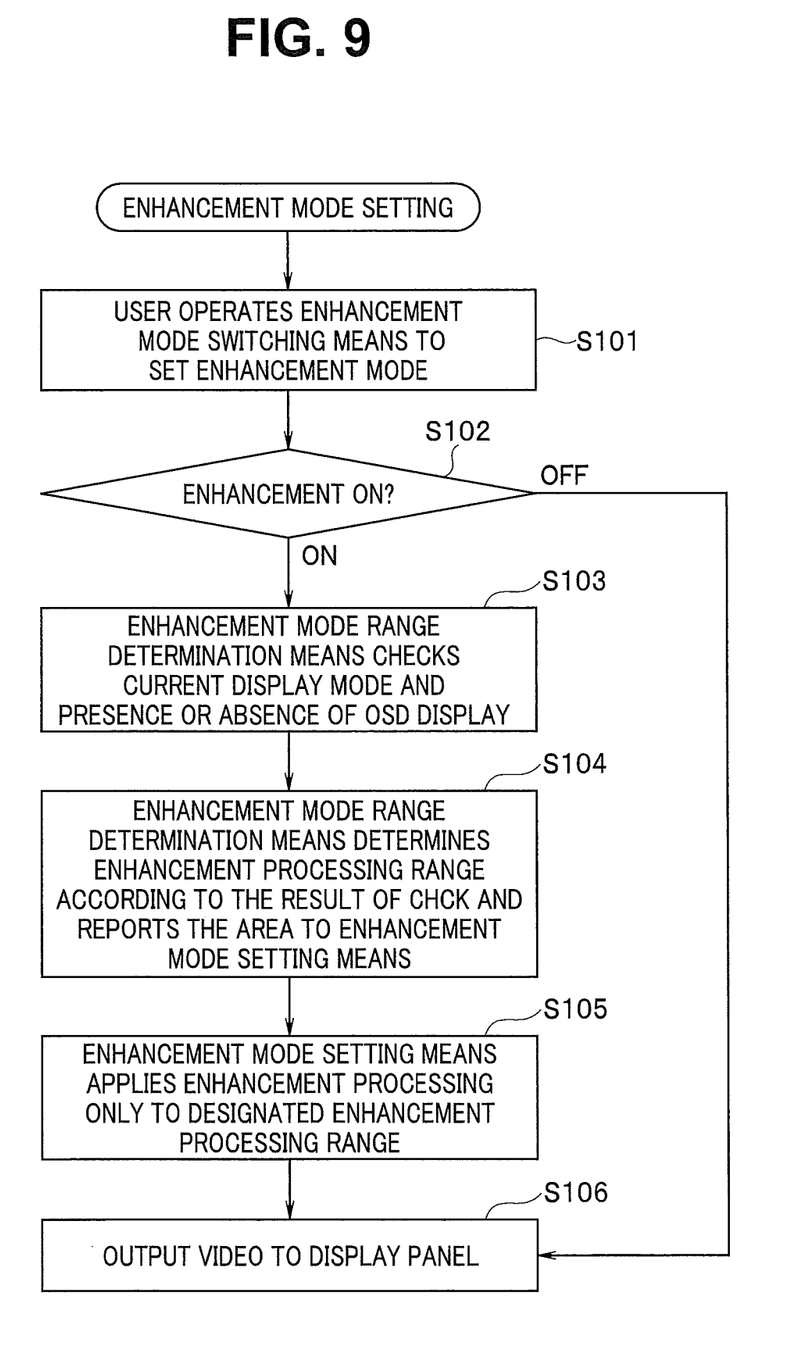
FIG. 9 is a flowchart showing an action when an enhancement mode is set in the monitor apparatus of the endoscopic operation system according to the second embodiment of the present invention.

FIG. 9 is a flowchart showing an action when the enhancement mode is set in the monitor apparatus of the endoscopic operation system according to the second embodiment.

As shown in FIG. 9, after a user operates the enhancement mode switching means to set the enhancement mode (step S101), predetermined enhancement processing operation is performed (step S102), and the enhancement mode range determination means 163 checks the current display mode in the display mode setting means 161 and the presence or absence of the OSD display in the signal processing section 140 (step S103).

Subsequently, the enhancement mode range determination means 163 determines the enhancement processing range according to the result of the check in step S103 and reports the range (area) to the enhancement mode setting means 162 (step S104).

The enhancement mode setting means 162 applies the enhancement processing only to the designated enhancement processing range (step 105) and transmits the video signal after the enhancement processing to the display panel 153 (step S106).

As described, according to the present second embodiment, the range (area) of applying the enhancement processing can be set on the screen of the display panel according to the conditions of the display screen, that is, according to the current state of the display mode (one-screen display state or multiple-screen display state including two-screen) and the presence or absence of the OSD display. Therefore, if the enhancement processing is applied to an endoscopic image for example, the enhancement processing is not applied to a sub screen display area or an OSD display area displayed on the same screen, and easily viewable screen display can be provided.

Note that the present invention is not limited to the embodiments, and various changes, modifications, and the like can be obviously made without changing the scope of the present invention.

What is claimed is:

1. A monitor apparatus that is configured as a separate body from at least a video processor including a medical image processing section, and includes a housing in which a display section that displays a predetermined medical image is disposed, the monitor apparatus comprising:

the display section that displays a medical image;

a plurality of medical image signal input sections disposed in the housing of the monitor apparatus including the display section, each of the plurality of medical image signal input sections being capable of receiving a predetermined medical image signal including a medical image signal outputted from the video processor;

a signal processing section that is disposed in the housing of the monitor apparatus and applies predetermined signal processing to the medical image signal inputted to each of the medical image signal input sections, to generate a video signal to be displayed on the display section;

a first color setting reflection section that is disposed in the housing of the monitor apparatus and executes color adjustment processing by applying a predetermined first color setting to the video signal to be displayed on the display section which has been generated by the signal processing section;

a second color setting reflection section that is disposed in the housing of the monitor apparatus and executes color adjustment processing by applying a second color setting to the video signal to be displayed on the display section which has been generated by the signal processing section, wherein the second color setting is identical to the first color setting in the first color setting reflection section;

a video signal output section that is disposed in the housing of the monitor apparatus, the video signal output section being connected with at least one or more external devices and capable of outputting the video signal outputted from the second color setting reflection section; and an external device information detecting section that is disposed in the housing of the monitor apparatus and detects device information regarding a type of the external device connected to the video signal output section, wherein the second color setting reflection section executes, in accordance with the type of the external device, any one of:

first mode processing performing color adjustment processing based on the second color setting, which is the same color setting as the first color setting in the first color setting reflection section, on the video signal to be displayed on the display section which has been generated by the signal processing section such that a display color on the connected external device is the same as the display color of the display section, to cause the video signal output section to output the video signal;

second mode processing causing the video signal output section to output the video signal to be displayed on the display section which has been generated by the signal processing section, without performing any color adjustment processing on the video signal; and third mode processing performing color adjustment processing based on a third color setting set according to color setting included in the external device connected to the video signal output section, in addition to the second color setting, on the video signal to be displayed on the display section which has been generated by the video signal processing section, when the external device has a color setting function different from the first color setting, based on a detection result from the external device information detecting section, to cause the video signal output section to output the video signal.

2. The monitor apparatus according to claim 1, wherein the second color setting reflection section includes a color setting table including the color setting according to the type of the external device connected to the video signal output section, and when executing the third mode processing, the second color setting section sets the third color setting based on the color setting in the color setting table.

3. The monitor apparatus according to claim 1, wherein the external device information detecting section includes a communication section for communication between the monitor apparatus and the external device, and detects the device information regarding the type of the external device through the communication by the communication section.

4. The monitor apparatus according to claim 1, further comprising an operation section connected to the first color setting reflection section and the second color setting reflection section, wherein the operation section executes processing regarding the first color setting in the first color setting reflection section and processing regarding the second color setting in the second color setting reflection section.

5. A monitor apparatus configured as a separate body from at least a video processor including a medical image processing section, the monitor apparatus comprising:

a housing having a display that displays a predetermined medical image;

a plurality of medical image signal input sections disposed in the housing, each of the plurality of medical image signal input sections being capable of receiving a predetermined medical image signal including a medical image signal outputted from the video processor;

a video signal output section disposed in the housing, the video signal output section being connected with at least one or more external devices;

an external device information detecting section disposed in the housing, the external device information detecting section detecting device information regarding a type of the external device connected to the video signal output section;

a memory disposed in the housing of the monitor apparatus; and a processor disposed in the housing of the monitor apparatus, the processor being operatively coupled to the memory and being programmed to:
apply predetermined signal processing to the medical image signal inputted to each of the medical image signal input sections, to generate a video signal to be displayed on the display section;
execute color adjustment processing by applying a predetermined first color setting to the generated video signal to be displayed on the display section;
execute at least color adjustment processing by applying a second color setting to the generated video signal, the second color setting being identical to the first color setting, wherein:

the processor executes, in accordance with the type of the external device, any one of:
first mode processing performing color adjustment processing based on the second color setting, which is the same color setting as the first color setting, on the generated video signal to be displayed on the display section such that a display color on the connected external device is the same as the display color of the display section, and causing the video signal output section to output the processed video signal;
second mode processing causing the video signal output section to output the generated video signal to be displayed on the display section, without performing any color adjustment processing on the video signal; and
third mode processing performing color adjustment processing based on a third color setting that is set according to color setting information included in the external device connected to the video signal output section, in addition to the second color setting, on the generated video signal to be displayed on the display section, when the external device has a color setting function different from the first color setting, based on a detection result from the external device information detecting section, and causing the video signal output section to output the processed video signal.

6. The monitor apparatus according to claim 5, wherein the memory stores a color setting table including the color setting according to the type of the external device connected to the video signal output section, and when executing the third mode processing, the processor sets the third color setting based on the color setting in the color setting table.

7. The monitor apparatus according to claim 5, wherein the external device information detecting section is configured to:

provide communication between the monitor apparatus and the external device, and detect the device information regarding the type of the external device through the communication between the monitor apparatus and the external device.

\* \* \* \* \*

UNITED STATES PATENT AND TRADEMARK OFFICE
CERTIFICATE OF CORRECTION

| | |
|---|---|
| PATENT NO. | : 9,795,277 B2 |
| APPLICATION NO. | : 14/982543 |
| DATED | : October 24, 2017 |
| INVENTOR(S) | : Masaya Fujita et al. |

Page 1 of 1

It is certified that error appears in the above-identified patent and that said Letters Patent is hereby corrected as shown below:

Column 12, Claim 5, Line 62, delete "information".

Signed and Sealed this
Tenth Day of April, 2018

Andrei Iancu
*Director of the United States Patent and Trademark Office*